United States Patent
Mao et al.

(10) Patent No.: US 11,561,169 B2
(45) Date of Patent: Jan. 24, 2023

(54) METHOD FOR CONSTRUCTING WATER QUALITY INDEX PREDICTION MODELS AND METHOD FOR MONITORING WATER QUALITY INDEXES

(71) Applicant: Sichuan Belam Technology Co., Ltd., Mianyang (CN)

(72) Inventors: Benjiang Mao, Mianyang (CN); Hailin Chu, Mianyang (CN); Zancheng Jiang, Mianyang (CN); Yixin Liu, Mianyang (CN); Yikun Qian, Mianyang (CN)

(73) Assignee: Sichuan Belam Technology Co., Ltd., Mianyang (CN)

( * ) Notice: Subject to any disclaimer, the term of this patent is extended or adjusted under 35 U.S.C. 154(b) by 106 days.

(21) Appl. No.: 17/419,550

(22) PCT Filed: Jun. 13, 2019

(86) PCT No.: PCT/CN2019/091015
§ 371 (c)(1),
(2) Date: Jun. 29, 2021

(87) PCT Pub. No.: WO2020/133944
PCT Pub. Date: Jul. 2, 2020

(65) Prior Publication Data
US 2022/0146417 A1 May 12, 2022

(30) Foreign Application Priority Data
Dec. 29, 2018 (CN) .......................... 201811635500.7

(51) Int. Cl.
*G01N 21/3577* (2014.01)
*G01N 21/33* (2006.01)
*G01N 21/359* (2014.01)
*G01N 33/18* (2006.01)

(52) U.S. Cl.
CPC ......... *G01N 21/3577* (2013.01); *G01N 21/33* (2013.01); *G01N 21/359* (2013.01); *G01N 33/18* (2013.01)

(58) Field of Classification Search
CPC .. G01N 21/3577; G01N 21/33; G01N 21/359; G01N 33/18; G01N 21/94; G01N 21/31; G01N 2201/1296; G01N 1/44
See application file for complete search history.

(56) References Cited

U.S. PATENT DOCUMENTS

| | | | | |
|---|---|---|---|---|
| 10,302,552 | B2 * | 5/2019 | Rajasekharan | G01N 33/1806 |
| 2013/0268239 | A1 * | 10/2013 | Katsuyama | G01N 21/25 |
| | | | | 702/179 |
| 2015/0168366 | A1 * | 6/2015 | Volker | G01N 33/1806 |
| | | | | 422/549 |
| 2019/0049423 | A1 * | 2/2019 | Weindorf | G01N 23/223 |
| 2021/0208116 | A1 * | 7/2021 | Li | G01N 30/88 |

FOREIGN PATENT DOCUMENTS

| | | | | |
|---|---|---|---|---|
| CN | 101105439 | A | | 1/2008 |
| CN | 101907565 | A | | 12/2010 |
| CN | 203275288 | U | * | 11/2013 |
| CN | 104034684 | A | | 9/2014 |
| CN | 105651336 | A | | 6/2016 |
| CN | 106990060 | A | | 7/2017 |
| CN | 109540832 | A | * | 3/2019 ......... G01N 21/3577 |
| CN | 109709057 | A | | 5/2019 |
| CN | 106198424 | B | * | 3/2020 ............. G01N 21/31 |

OTHER PUBLICATIONS

English Abstract for CN 101105439 A (2008).
English Abstract for CN 101907565 A (2010).
English Abstract for CN 104034684 A (2014).
English Abstract for CN 105651336 A (2016).
English Abstract for CN 106990060 A (2017).
English Abstract for CN 109709057 A (2019).

* cited by examiner

*Primary Examiner* — Marcus H Taningco
(74) *Attorney, Agent, or Firm* — Caesar Rivise, PC

(57) ABSTRACT

The present invention relates to the field of environment monitoring. The present invention solves the problem in the prior art of large errors arising when using spectrophotometry to monitor a water quality COD index, and provides a method for constructing a water quality index prediction model and a method for monitoring a water quality index. The technical solution thereof can be summarized as follows: a method for constructing a water quality index prediction model, comprising: acquiring multiple water samples as water inspection samples, and acquiring respective required water quality indexes for the water inspection samples; measuring, for each of the water inspection samples, a spectrum corresponding thereto, obtaining an original spectrum, and acquiring a physical parameter thereof; conducting at least two digestions on the water inspection samples, measuring a spectrum corresponding thereto after each of the digestions to obtain a digestion spectrum, and acquiring a digestion parameter of the digestion and a physical parameter of the water inspection samples after the digestion; and independently constructing, according to data collected from each of the water inspection samples, an individual water quality index prediction model for each of the required water quality indexes. The present invention has an advantageous effect of fundamentally reducing measurement errors, and is applicable to water quality index monitoring.

9 Claims, No Drawings

METHOD FOR CONSTRUCTING WATER QUALITY INDEX PREDICTION MODELS AND METHOD FOR MONITORING WATER QUALITY INDEXES

CROSS-REFERENCE TO RELATED APPLICATIONS

This application is a U.S. National Phase application of PCT/CN2019/091015, filed Jun. 13, 2019, which claims priority to CN 201811635500.7, filed Dec. 29, 2018, the contents of which applications are incorporated herein by reference in their entireties for all purposes.

FIELD OF THE INVENTION

The present invention relates to the field of environmental monitoring, particularly to a method for monitoring water quality indexes in real time.

BACKGROUND OF THE INVENTION

At present, common water quality indexes such as chemical oxygen demand (COD), ammonia nitrogen (AN), total phosphorus (TP) and total nitrogen (TN) for measuring environmental water quality in China are measured by methods specified in national standards. Almost all of these analysis methods require chemical reagents, and produce effluent. The chemical reagents used and the effluent produced often contains toxic heavy metals such as chromium and mercury, and heavy metals such as silver, manganese, molybdenum, etc. It is estimated that the effluent produced by the water quality monitors alone reaches nearly 100,000 tons every year in China, and the environmental risks cannot be ignored.

In order to overcome the disadvantages of conventional chemical analysis methods, the UV spectroscopy invented in the 1960s to monitor the COD index has attracted increasing attention, especially the COD measurement technology using multi-wavelength or even the whole UV-visible spectrum which has been developed rapidly in recent years. The method has the advantage of fast analysis speed, generally about 10 seconds, and does not need any toxic chemical reagents such as potassium dichromate, mercury sulfate, silver sulfate, etc. Thereby avoiding the environmental risk of secondary pollution. This provides a promising alternative to the widely used COD chemical analysis method, and the economic and environmental benefits are very attractive.

The COD monitoring technology by UV-visible spectrometry is to obtain UV-visible absorption spectra of water samples by transmitting light beams through the water samples to be measured, and obtain the mathematical relationship, i.e., a mathematical model for COD measurement, between COD index and spectral data of the water samples by a regression algorithm by using the known COD index and UV-visible absorption spectral data of a plurality of water samples; and then calculate the COD index of the water samples to be measured based on the mathematical model for COD measurement by measuring the UV-visible spectral data of unknown water samples. However, since the existing monitoring methods, technologies and instruments are based on working modes of single machine, and the type and quantity of water samples used in COD measurement (i.e., prediction) models in the instruments are limited, it is often impossible to give accurate COD measurements when the composition of the water samples changes greatly. Some organic substances composed of single bonds such as C—C, C—H and N—H, and some inorganic reducing substances have no absorption peaks in the UV-visible wavelength range of 200 nm-780 nm, which leads to measurement errors and limits the scope of application of existing COD measuring instruments by UV-visible spectroscopy.

In order to make up for the defects in the prior art, unremitting efforts have been made in UV-visible spectroscopy, optimization algorithms of mathematical models for COD measurement and classification of water samples. For example, in the invention patent with patent number of 201710183620.7, foreground-background interaction of monitoring data is realized through the Internet of Things by methods such as water sample type identification and remote water sample database, greatly improving the adaptability of COD spectrometry to different types of water quality. Although other existing water quality indexes such as permanganate, nitrate and turbidity can be monitored in the same way, a plurality of water quality index monitors are required to test the indexes respectively, that is, each index corresponds to a water quality index monitor.

SUMMARY OF THE INVENTION

The present invention provides a method for constructing water quality index prediction models and a method for monitoring water quality indexes with the purpose of overcoming the defects that there are large errors in monitoring COD index by spectroscopy, and ammonia nitrogen, total phosphorus and total nitrogen cannot be measured directly by UV-visible spectroscopy at the same time.

The technical solution for solving the technical problem of the present invention is a method for constructing water quality index prediction models, characterized by comprising the following steps:

Step 1. collecting different types of water samples at different water quality index concentrations as water samples, and acquiring required water quality indexes of each water sample respectively, wherein at least one of the required water quality indexes is acquired;

Step 2. measuring the corresponding spectrum for each water sample to acquire an original spectrum, and acquiring the corresponding physical parameters;

Step 3. digesting the water sample at least twice, and measuring the corresponding spectrum once for each digestion to acquire the corresponding digestion spectrum, as well as digestion parameters for each digestion and physical parameters of the water sample after each digestion; and Step 4. constructing a water quality index prediction model for each required water quality index according to the original spectrum, the digestion parameters, the corresponding physical parameters, the corresponding digestion spectrum and the required water quality indexes of each water sample.

Specifically, in order to present several common water quality indexes, in Step 1, the required water quality indexes preferably comprise COD and/or AN and/or TP and/or TN; and In Step 4, the water quality index prediction model is a COD prediction model and/or an AN prediction model and/or a TP prediction model and/or a TN prediction model.

Further, in Step 2 and Step 3, the corresponding spectra are UV-visible absorption spectra and near-infrared absorption spectra. The absorption spectra are commonly used in the monitoring field, which can save system development costs.

Further, in Step 3, the digestion is wet digestion, electrochemical digestion or UV digestion or microwave digestion.

The digestion methods are the existing digestion methods, which can save system development costs.

Specifically, in Step 3, the digestion parameters comprise selected reagents, digestion time and pressure when the digestion is wet digestion.

The digestion parameters comprise pH, electrode area, voltage, current and digestion time when the digestion is electrochemical digestion.

The digestion parameters are also the necessary digestion parameters for wet digestion and electrochemical digestion in the prior art, and thus is not repeated herein.

Further, in Step 3, the digestion rate for target contaminants in each of the at least two digestion is lower than 100%, because the target contaminants disappear if the digestion rate is up to 100%, then the data is meaningless.

Specifically, in Step 2 and Step 3, the water samples are put into an optical measuring cell for measurement; and In Step 3, the water samples are put into a digestion cuvette for digestion.

The purpose is to maintain the same environment for each measurements of each water sample.

Further, in order to explain the physical parameters, the physical parameters in Step 2 and Step 3 comprise pH, temperature, turbidity, conductivity and dissolved oxygen.

A method for monitoring water quality indexes, comprising the following steps:

A. acquiring a spectrum corresponding to a water sample to be tested to acquire an original spectrum of the water sample to be tested;

B. digesting the water sample to be tested at least once, and measuring the corresponding spectrum once for each digestion to acquire the corresponding digestion spectrum of the water sample to be tested, as well as digestion parameters for each digestion and physical parameters of the water sample to be tested after each digestion; and C. substituting the original spectrum of the water sample to be tested, the digestion parameters for each digestion, the corresponding physical parameters and the corresponding digestion spectrum into each of the water quality index prediction models to obtain predicted results of the water quality indexes respectively, i.e., monitoring results of the water quality indexes.

Specifically, in order to improve the monitoring accuracy, the corresponding spectrum, method for digestion, selection of digestion parameters, selection of physical parameters, and environment for measurement and digestion correspond to those for constructing the water quality index prediction models respectively.

The advantageous effects of the present invention are as follows: the method for constructing water quality index prediction models and the method for monitoring water quality indexes allow substances that are not directly measurable (here, measurement refers to be represented spectroscopically) in water samples (including water samples and water samples to be tested) to be measurable due to digestion, thereby reducing measurement errors fundamentally. In addition, multispectral information of the water samples be obtained by cascading multiple digestion and keeping the digestion rate below 100%. Characteristic parameters of water quality indexes can be extracted by using such spectral information, and a variety of water quality index prediction models can be established based on the characteristic parameters, so that required water quality indexes can be measured based on a set of measurement data in actual measurement, thereby reducing the quantity of water quality index monitors and monitoring steps.

DETAILED DESCRIPTION OF THE PREFERRED EMBODIMENTS

The technical solution of the present invention will be described in detail with reference to embodiments.

The method for constructing water quality index prediction models, comprising the following steps:

Step 1. collecting different types of water samples at different water quality index concentrations as water samples, and acquiring required water quality indexes of each water sample respectively, wherein at least one of the required water quality indexes is acquired;

Step 2. measuring the corresponding spectrum for each water sample to acquire an original spectrum, and acquiring the corresponding physical parameters;

Step 3. digesting the water sample at least twice, and measuring the corresponding spectrum once for each digestion to acquire the corresponding digestion spectrum, as well as digestion parameters for each digestion and physical parameters of the water sample after each digestion;

Step 4. constructing a water quality index prediction model for each required water quality index according to the original spectrum, the digestion parameters, the corresponding physical parameters, the corresponding digestion spectrum and the required water quality indexes of each water sample.

In order to present several common water quality indexes, in Step 1, the required water quality indexes preferably comprise COD and/or AN and/or TP and/or TN;

Correspondingly, in Step 4, the water quality index prediction model is a COD prediction model and/or an AN prediction model and/or a TP prediction model and/or a TN prediction model.

Of course, water quality indexes can further comprise permanganate index, nitrate nitrogen and nitrite nitrogen, biochemical oxygen demand, total organic carbon, dissolved organic matter, turbidity, chromaticity and so on.

In Step 2 and Step 3, the corresponding spectra are preferably UV-visible absorption spectra and near-infrared absorption spectra. The absorption spectra are commonly used in the monitoring field, which can save system development costs.

In Step 3, the digestion can be wet digestion, electrochemical digestion, UV digestion or microwave digestion. The digestion methods are the existing digestion methods, which can save system development costs.

In Step 3, the digestion parameters can comprise selected reagents, digestion time and pressure when the digestion is wet digestion; and The digestion parameters can comprise pH, electrode area, voltage, current and digestion time when the digestion is electrochemical digestion.

The digestion parameters are also the necessary digestion parameter for wet digestion and electrochemical digestion in the prior art, and thus is not repeated herein.

In Step 3, the digestion rate for target contaminants in each of the at least two digestion is lower than 100%, because the target contaminants disappear if the digestion rate is up to 100%, then the data is meaningless.

In Step 2 and Step 3, the water samples are put into an optical measuring cell for measurement; and In Step 3, the water samples are put into a digestion cuvette for digestion.

The purpose is to maintain the same environment for each measurements of each water sample.

In order to explain the physical parameters, the physical parameters in Step 2 and Step 3 preferably comprise pH, temperature, turbidity, conductivity and dissolved oxygen.

The method for monitoring water quality indexes provided by the present invention comprises the following steps:

A. acquiring a spectrum corresponding to a water sample to be tested to acquire an original spectrum of the water sample to be tested;

B. digesting the water sample to be tested at least once, and measuring the corresponding spectrum once for each digestion to acquire the corresponding digestion spectrum of the water sample to be tested, as well as digestion parameters for each digestion and physical parameters of the water sample to be tested after each digestion; and C. substituting the original spectrum of the water sample to be tested, the digestion parameters for each digestion, the corresponding physical parameters and the corresponding digestion spectrum into each of the above water quality index prediction models to obtain predicted results of the water quality indexes respectively, i.e., monitoring results of the water quality indexes.

In order to improve the monitoring accuracy, the corresponding spectrum, method for digestion, selection of digestion parameters, selection of physical parameters, and environment for measurement and digestion correspond to those for constructing the water quality index prediction models respectively, that is:

If the corresponding spectra are UV-visible absorption spectra and near-infrared absorption spectra when a water quality index prediction model is constructed, the corresponding spectra are also UV-visible absorption spectra and near-infrared absorption spectra during monitoring;

If the digestion method used in the construction of a water quality index prediction model is wet digestion and digestion parameters comprise selected reagents, digestion time and pressure, the digestion method used during monitoring is also wet digestion and digestion parameters comprise selected reagents, digestion time and pressure. The same is true when the digestion method is electrochemical digestion. If multiple digestion methods are used in the construction of a water quality index prediction model, any of the digestion methods can be selected according to the actual situation during monitoring. It should be noted here that in order to improve the accuracy of measurement, only the method for digestion and selection of digestion parameters are required to correspond to each other, and specific values of digestion parameters during tests are not required to be the same as those in the construction of a water quality index prediction model.

If the physical parameters are pH, temperature, turbidity, conductivity and dissolved oxygen in the construction of a water quality index prediction model, the physical parameters during monitoring are at least one or all of pH, temperature, turbidity, conductivity and dissolved oxygen, preferably the same. Similarly, it should be noted that in order to improve the accuracy of measurement, only the selection of physical parameters is required to correspond to each other, and specific values of physical parameters during tests are not required to be the same as those in the construction of a water quality index prediction model;

If the water samples are put into an optical measuring cell for measurement and put into a digestion cuvette for digestion in the construction of a water quality index prediction model, the water samples should also be put into the optical measuring cell for measurement and put into the digestion cuvette for digestion during monitoring to improve the accuracy of monitoring.

EXAMPLE

In the example, COD, AN, TP and TN are taken as examples of required water quality indexes to describe in detail how to construct water quality index prediction models in Step 4.

In the construction of a water quality index prediction model, assuming that a total of m water samples are collected and the $i^{th}$ water sample needs to be digested for n times, then i=1, 2, . . . , m; the UV-visible absorption spectrum is $S_{uvij}$ and the near-infrared absorption spectrum is $S_{nrij}$ at the $j^{th}$ digestion, j=0, 1, 2, . . . , n; when j=0, the absorption spectrum is the original UV-visible absorption spectrum $S_{uvi0}$ and the original near-infrared absorption spectrum $S_{nvi0}$ of the water sample. Similarly, the digestion parameter is recorded as $D_{ij}$, the physical parameter is recorded as $P_{ij}$, and required water quality indexes are $COD_i$, $AN_i$, $TP_i$ and $TN_i$ respectively. It should be noted here that when j=0, $D_{i0}$ and $P_{i0}$ are not recorded.

Then cascade sample arrays $B_{1 \times T} = [S_{nrij}, S_{uvij}, D_{ij}, P_{ij}]_{1 \times T}$ (j=0, 1, 2, . . . , n) and $[COD_i, AN_i, TP_i, TN_i]_{1 \times 4}$ of the water sample can be constructed, where $T=(n+1) \times (N_{nr} + N_{uv}) + n \times (N_D + N_P)$, $N_{nr}$ is the data dimension of the near-infrared absorption spectrum, $N_{uv}$ is the data dimension of UV-visible spectrum, $N_D$ is the data dimension of the digestion parameter of the water sample, and $N_P$ is the data dimension of the physical parameter of the water sample.

Then sample data of the m water samples are combined to obtain a sample data matrix $B_{m \times T} = [S_{nr0}, S_{nrj}, S_{uv0}, S_{uvj}D_j, P_j]_{m \times T}$ (j=1, 2, . . . , n), $[COD, AN, TP, TN]_{m \times 4}$.

With $B_{m \times T}$ in the sample data matrix as an input and $[COD, AN, TP, TN]_{m \times 4}$ as an output of models, a water quality COD prediction model=$f_1(B)$, an water quality AN prediction model=$f_2(B)$, a water quality TP prediction model=$f_3(B)$ and a water quality TN prediction model=$f_4(B)$ are built respectively by a mathematical modeling method, wherein, B represents the cascade sample array $B = [S_{nrij}, S_{uvij}, D_{ij}, P_{ij}]_{1 \times T}$ (j=0, 1, 2, . . . , x) of the water sample to be tested, and the x means that the water sample to be tested has been digested for x times in total.

The mathematical modeling method described here can be a commonly used multivariate nonlinear fitting modeling method such as least squares, or a machine learning modeling method such as neural network and support vector machine in the prior art, and thus is not repeated herein.

In addition, in the example of the present invention, a monitoring system can be built by the method described in the invention with patent number of 201710183620.7, and an optical measuring cell and a digestion cuvette can be provided to allow the monitoring to be more accurate in the actual monitoring.

The invention claimed is:

1. A method for constructing water quality index prediction models, comprising the following steps:
   Step 1. collecting different types of water samples at different water quality index concentrations as water samples, and acquiring required water quality indexes of each water sample respectively, wherein at least one of the required water quality indexes is acquired;
   Step 2. measuring a corresponding spectrum for each water sample to acquire an original spectrum, and acquiring corresponding physical parameters;

Step 3. digesting each water sample at least twice, and measuring the corresponding spectrum once for each digestion to acquire a corresponding digestion spectrum, as well as digestion parameters for each digestion and physical parameters of each water sample after each digestion; and Step 4. constructing a water quality index prediction model for each required water quality index according to the original spectrum, the digestion parameters, the corresponding physical parameters, the corresponding digestion spectrum and the required water quality indexes of each water sample.

2. The method for constructing water quality index prediction models according to claim 1, wherein in Step 1, the required water quality indexes comprise at least one of chemical oxygen demand (COD), ammonia nitrogen (AN), total phosphorus (TP) and total nitrogen (TN); and in Step 4, the water quality index prediction model is at least one of a COD prediction model, an AN prediction model, a TP prediction model and a TN prediction model.

3. The method for constructing water quality index prediction models according to claim 1, wherein in Step 2 and Step 3, the corresponding spectra are UV-visible absorption spectra and near-infrared absorption spectra.

4. The method for constructing water quality index prediction models according to claim 1, wherein in Step 3, the digestion is wet digestion, electrochemical digestion, UV digestion or microwave digestion.

5. The method for constructing water quality index prediction models according to claim 4, wherein in Step 3, the digestion parameters comprise selected reagents, digestion time and pressure when the digestion is wet digestion; and the digestion parameters comprise pH, electrode area, voltage, current and digestion time when the digestion is electrochemical digestion.

6. The method for constructing water quality index prediction models according to claim 1, wherein in Step 3, a digestion rate for target contaminants in each of the at least two digestions is lower than 100%.

7. The method for constructing water quality index prediction models according to claim 1, wherein in Step 2 and Step 3, the water samples are put into an optical measuring cell for measurement; and in Step 3, the water samples are put into a digestion cuvette for digestion.

8. A method for monitoring water quality indexes, comprising the following steps:

A. acquiring a spectrum corresponding to a water sample to be tested to acquire an original spectrum of the water sample to be tested;

B. digesting the water sample to be tested at least once, and measuring the corresponding spectrum once for each digestion to acquire the corresponding digestion spectrum of the water sample to be tested, as well as digestion parameters for each digestion and physical parameters of the water sample to be tested after each digestion; and C. substituting the original spectrum of the water sample to be tested, the digestion parameters for each digestion, the corresponding physical parameters and the corresponding digestion spectrum into a water quality index prediction model according to claim 1 to obtain predicted results of the water quality indexes respectively.

9. The method for monitoring water quality indexes according to claim 8, wherein the corresponding spectrum, method for digestion, selection of digestion parameters, selection of physical parameters, and environment for measurement and digestion correspond to those for constructing the water quality index prediction model.

* * * * *